US00PP13970P29

(12) United States Plant Patent
Bergman

(10) Patent No.: US PP13,970 P2
(45) Date of Patent: Jul. 15, 2003

(54) CHRYSANTHEMUM PLANT NAMED 'YOAMARILLO'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,317

(22) Filed: Mar. 8, 2002

(51) Int. Cl.[7] ..... A01H 5/00
(52) U.S. Cl. ..... Plt./289

(58) Field of Search ..... Plt./289, 287

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Yoamarillo', characterized by its uniform and upright plant habit; strong and freely branching growth habit; dense dark green foliage; uniform and early flowering habit; large decorative-type inflorescences with bright yellow-colored ray florets; excellent postproduction longevity with plants maintaining good substance and color for about four weeks in an interior environment; and tolerance to high production temperatures.

1 Drawing Sheet

BOTANICAL CLASSIFICATION/CULTIVAR DESIGNATION

*Chrysanthemum×morifolium* cultivar Yoamarillo.

BACKGROUND OF THE INVENTION

The present Invention relates to a new and distinct cultivar of Chrysanthemum plant, botanically known as *Chrysanthemum×morifolium* and hereinafter referred to by the name 'Yoamarillo'.

The new Chrysanthemum is a product of a planned breeding program conducted by the Inventor in Salinas, Calif. and Fort Myers, Fla. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in November, 1997, in Salinas, Calif., of a proprietary Chrysanthemum seedling selection identified as code number YB-4620, not patented, as the female, or seed, parent with a proprietary Chrysanthemum seedling selection identified as code number YB-5334, not patented, as the male, or pollen, parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and ray floret color, fast response time, and excellent postproduction longevity.

Asexual reproduction of the new Chrysanthemum by vegetative tip cuttings was first conducted in Fort Myers, Fla. in February, 1999. Asexual reproduction by cuttings has shown that the unique features of this new Chrysanthemum are stable and reproduced true to type in successive generations.

SUMMARY OF THE INVENTION

The cultivar Yoamarillo has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yoamarillo'. These characteristics in combination distinguish 'Yoamarillo' as a new and distinct Chrysanthemum:

1. Uniform and upright plant habit.
2. Strong and freely branching growth habit.
3. Dense dark green foliage.
4. Uniform flowering habit.
5. Early flowering, eight-week response time.
6. Large decorative-type inflorescences.
7. Bright yellow-colored ray florets.
8. Excellent postproduction longevity with plants maintaining good substance and color for about four weeks in an interior environment.
9. Tolerance to high production temperatures.

Plants of the new Chrysanthemum differ primarily from plants of the female parent selection in ray floret coloration as plants of the new Chrysanthemum have bright yellow-colored ray florets whereas plants of the female parent selection have light bronze-colored ray florets.

Plants of the new Chrysanthemum differ primarily from plants of the male parent selection in ray floret coloration as plants of the new Chrysanthemum have bright yellow-colored ray florets whereas plants of the male parent selection have white-colored ray florets.

Plants of the new Chrysanthemum can be compared to plants of the cultivar Yotopeka, disclosed in U.S. Plant Pat. No. 11,210. In side-by-side comparisons conducted by the Inventor in Salinas, Calif., plants of the new Chrysanthemum differed from plants of the cultivar Yotopeka in the following characteristics:

1. Plants of the new Chrysanthemum were more upright and not as outwardly spreading as plants of the cultivar Yotopeka.

2. Plants of the new Chrysanthemum had larger inflorescences than plants of the cultivar Yotopeka.

3. Ray floret color of plants of the new Chrysanthemum was brighter yellow than ray floret color of plants of the cultivar Yotopeka.

4. Plants of the new Chrysanthemum were more tolerant to high production temperatures than plants of the cultivar Yotopeka.

5. Plants of the new Chrysanthemum lasted about one week longer in an interior environment than plants of the cultivar Yotopeka.

Plants of the new Chrysanthemum can also be compared to plants of the cultivar Yellow Diamond, disclosed in U.S. Plant Pat. No. 8,364. In side-by-side comparisons conducted by the Inventor in Salinas, Calif., plants of the new Chrysanthemum differed from plants of the cultivar Yellow Diamond in the following characteristics:

1. Plants of the new Chrysanthemum were more upright and vigorous than plants of the cultivar Yellow Diamond.

2. Plants of the new Chrysanthemum had darker green foliage than plants of the cultivar Yellow Diamond.

3. Plants of the new Chrysanthemum had smaller inflorescences than plants of the cultivar Yellow Diamond.

4. Ray floret color of plants of the new Chrysanthemum was brighter yellow than ray floret color of plants of the cultivar Yellow Diamond.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a side perspective view of a typical flowering plant of 'Yoamarillo' grown as a disbud-type.

The photograph at the bottom of the sheet comprises a close-up view of typical inflorescences of 'Yoamarillo' grown as a disbud-type.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 footcandles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as disbud-types. Measurements and numerical values represent averages of typical flowering plants.

Botanical classification: *Chrysanthemum×morifolium* cultivar Yoamarillo.

Commercial classification: Decorative-type potted Chrysanthemum.

Parentage:

*Female, or seed, parent.*—Proprietary *Chrysanthemum×morifolium* seedling selection identified as code number YB-4620, not patented.

*Male, or pollen, parent.*—Proprietary *Chrysanthemum×morifolium* seedling selection identified as code number YB-5334, not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous decorative-type potted Chrysanthemum that can be grown as a disbud or as a spray-type. Stems mostly upright and somewhat outwardly spreading; uniform crown. Freely branching, about three to four lateral branches develop after removal of terminal apex (pinching); dense and full plants.

*Plant height.*—About 29 cm.

*Plant width.*—About 41 cm.

*Lateral branches* (*peduncles*).—Length: About 20 cm. Diameter: About 4 mm. Internode length: About 1.5 cm. Strength: Strong. Texture: Pubescent. Color: 146A.

*Foliage description.*—Arrangement: Alternate. Length: About 7.5 cm. Width: About 6.7 cm. Apex: Cuspidate to mucronate. Base: Truncate. Margin: Palmately lobed, sinuses between lateral lobes convergent. Texture: Upper surface: Sparsely pubescent. Lower surface: Pubescent; veins prominent. Color: Young and mature foliage, upper surface: 147A. Young and mature foliage, lower surface: Close to 147B. Venation, upper surface: Close to 147A to 147B. Venation, lower surface: Close to 146B. Petiole length: About 3.4 cm. Petiole diameter: About 3 mm. Petiole color, both surfaces: Close to 146B.

Inflorescence description:

*Appearance.*—Decorative-type inflorescence form with elongated oblong and spoon-shaped ray florets. Inflorescences borne on terminals above foliage. Disk and ray florets arranged acropetally on a capitulum. Not fragrant. Can be grown as a disbud or spray-type. Flowering response: Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for at about four weeks in an interior environment.

*Quantity of inflorescences.*—Grown as a disbud-type, only one inflorescence, the terminal inflorescence, develops per lateral branch.

*Inflorescence bud.*—Height: About 8 mm. Diameter: About 9 mm. Shape: Oblate. Color: Between 146A and 147A.

*Inflorescence size.*—Diameter: About 11.3 cm. Depth (height): About 3 cm. Diameter of disc: About 2 mm, inconspicious. Receptacle diameter: About 7.5 mm.

*Ray florets.*—Shape: Elongated-oblong or spoon-shaped. Orientation: Initially upright, then perpendicular to the peduncle. Aspect: Initially slightly incurved, then mostly flat. Length: About 5.5 cm. Width: About 1.1 cm. Apex: Emarginate. Base: Fused into a corolla tube. Corolla tube length: Variable, about 1.1 to 3.7 cm. Margin: Entire. Texture: Smooth, glabrous, satiny. Number of ray florets per inflorescence: About 224 arranged in numerous rows. Color: When opening, upper and lower surfaces: 9A. Fully expanded, upper surface: 9A. Fully expanded, lower surface: Close to 4B to 5C.

*Disc florets.*—Arrangement: Massed at center of receptacle. Shape: Tubular, elongated. Apex: Five-pointed. Length: About 7 mm. Width: Apex: About 1.5 mm. Base: About 1 mm. Number of disc florets per inflorescence: Less than 10 to none. Color: Immature: 154D. Mature: Apex: Close to 13A. Mid-section and base: Close to 150D.

*Phyllaries.*—Quantity per inflorescence: About 25. Length: About 8 mm. Width: About 3 mm. Shape: Ligulate. Apex: Acute. Base: Truncate. Texture: Upper surface: Waxy, smooth. Lower surface: Pubescent. Color: Upper surface: Close to 146A. Lower surface: Between 147A and 146A.

*Reproductive organs.*—Androecium: Present on disc florets only. Anther color: 12A. Pollen amount: None observed. Gynoecium: Present on both ray and disc florets. Style color: Close to 150D. Stigma color: Close to 12A.

*Seed.*—Seed production has not been observed.

Disease resistance: Resistance to pathogens common to Chrysanthemums has not been observed on plants grown under commercial greenhouse conditions.

High temperature tolerance: Plants of the new Chrysanthemum have been observed to be tolerant to high temperature conditions when grown during the summer under greenhouse conditions in southwest Florida.

It is claimed:

1. A new and distinct cultivar of Chrysanthemum plant named 'Yoamarillo', as illustrated and described.

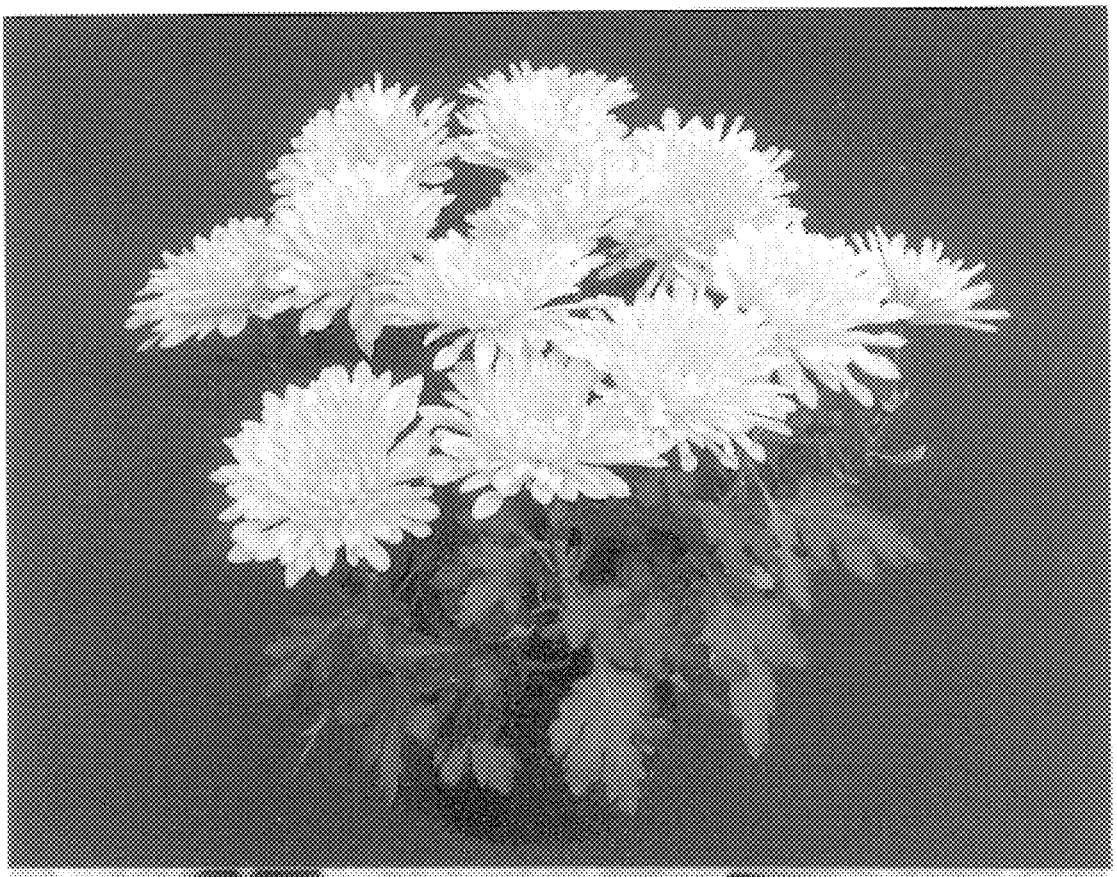
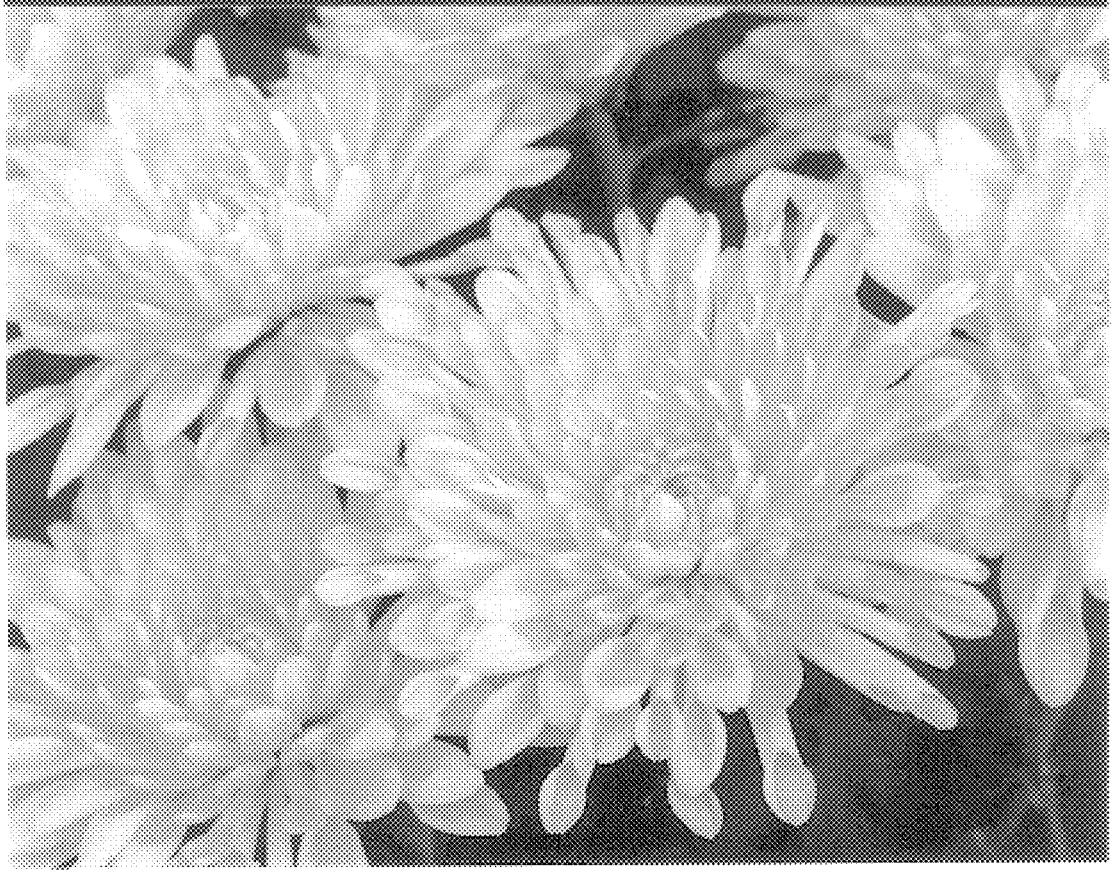

* * * * *